(12) United States Patent
Yang et al.

(10) Patent No.: US 8,330,604 B2
(45) Date of Patent: Dec. 11, 2012

(54) HANDHELD SALINITY ANALYZER

(75) Inventors: Gil mo Yang, Suwon-si (KR); Eun gi Cho, Hwaseong-si (KR); Kang jin Lee, Hwaseong-si (KR); Gi young Kim, Seoul (KR); Jae yong Son, Suwon-si (KR); Suk won Kang, Seoul (KR); Chang yeun Mo, Bucheon-si (KR); Jai gyu Kim, Suwon-si (KR); In ho Seo, Anyang-si (KR)

(73) Assignees: Dae Yoon Scale Industrial Co., Ltd., Seoul (KR); Republic of Korea (Management: Rural Development Administration), Suwon-Si (KR)

( * ) Notice: Subject to any disclaimer, the term of this patent is extended or adjusted under 35 U.S.C. 154(b) by 450 days.

(21) Appl. No.: 12/725,312

(22) Filed: Mar. 16, 2010

(65) Prior Publication Data
US 2011/0018725 A1    Jan. 27, 2011

(30) Foreign Application Priority Data
Jul. 21, 2009   (KR) ......................... 10-2009-0066472

(51) Int. Cl.
*G08B 21/00* (2006.01)
(52) U.S. Cl. ............. 340/627; 99/324; 99/342; 324/446
(58) Field of Classification Search .................. 340/627, 340/584; 99/324; 324/446
See application file for complete search history.

(56) References Cited

U.S. PATENT DOCUMENTS

| | | | | |
|---|---|---|---|---|
| 4,331,923 A | * | 5/1982 | Akers, Jr. ...................... | 324/449 |
| 4,918,391 A | * | 4/1990 | Byrd ............................. | 324/446 |
| 7,183,779 B2 | * | 2/2007 | Hughes ......................... | 324/696 |
| 2006/0139037 A1 | * | 6/2006 | Hughes ......................... | 324/696 |
| 2007/0048224 A1 | * | 3/2007 | Howell et al. .................. | 424/9.1 |

* cited by examiner

*Primary Examiner* — Albert Wong
*Assistant Examiner* — Rufus Point
(74) *Attorney, Agent, or Firm* — Kile Park Goekjian Reed & McManus PLLC (57) ABSTRACT

Disclosed is a handheld salinity analyzer including a body, in which a circuit board and a battery are installed, a cell block provided with one end inserted into one end of the body and the other end on which a projecting part provided with a salinity sensor hole and a depressed part provided with a temperature sensor hole are formed, a salinity sensor inserted into the salinity sensor hole and provided with one end connected to the circuit board, a temperature sensor inserted into the temperature sensor hole and provided with one end connected to the circuit board, an ON/OFF switch installed on the end of the body, a light emitting lamp connected to the circuit board, and a body cover connected to the end of the body provided with the ON/OFF switch or to the cell block, and provided with an operating piece to operate the ON/OFF switch.

5 Claims, 7 Drawing Sheets

HANDHELD SALINITY ANALYZER

BACKGROUND OF THE INVENTION

1. Field of the Invention

The present invention relates to a handheld salinity analyzer, and more particularly to a handheld salinity analyzer which is conveniently portable, does not consume power of a battery unnecessarily, rapidly and correctly measures the temperature of a food sample, and simply judges whether or not measured salinity of the food sample is less than or more than a set value.

2. Description of the Related Art

Salt is an essential flavoring enhancing the taste of food. The taste of food is generally measured through a sensory test by a person in charge of cooking of food in the kitchen.

Nowadays, recipes and feeding behavior have been diversified, and cooking techniques have changed so as to satisfy large-scale and industrialized trends, or have been standardized. During the standardization process of the cooking techniques, it is essentially required to indicate salinity of food, and particularly, of soup as an objective index.

As a conventional salinity measurement technique, a pulsating current flowing through a salinity analyzer is amplified and charges an integral condenser, integral current of the condenser is applied to one terminal of a comparator for a designated time and amplified current detected by a temperature sensor is applied to the other terminal of the comparator so as to obtain a temperature-compensated salinity current at an output terminal of the comparator, output of the comparator is converted into a digital value by an A/D converter through a buffer, and the digital value is displayed as a digit value by an LCD module.

Figure 1:
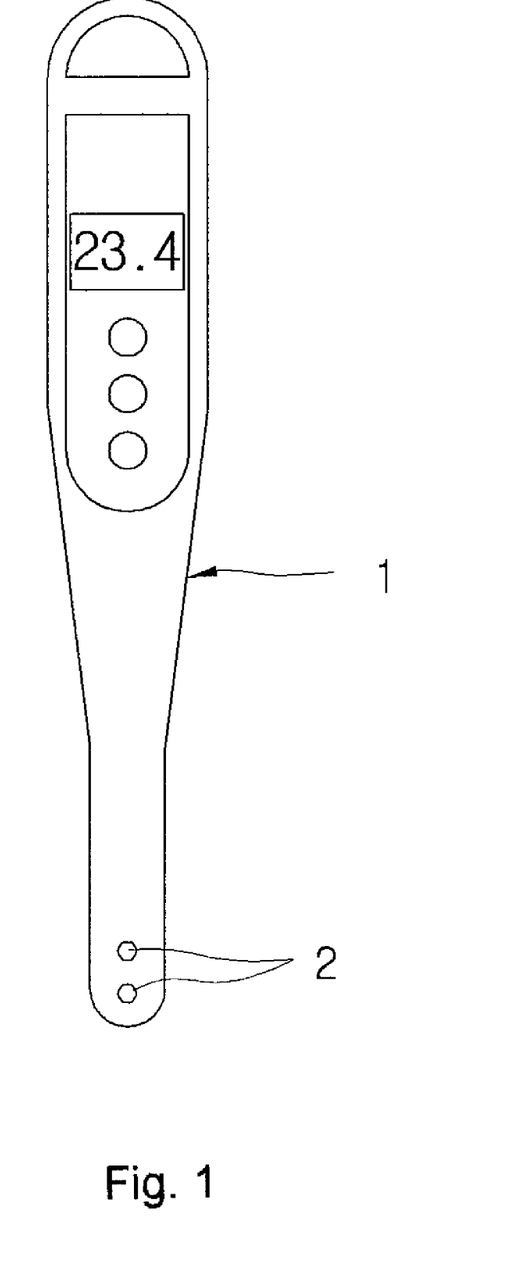
FIG. 1 is a schematic front view of a conventional salinity analyzer.

FIG. 1 is a schematic front view of such a conventional salinity analyzer so as to describe problems of the conventional salinity analyzer. Such a conventional salinity analyzer includes a case assembly 1 including a front case and a rear case, in which plural parts are mounted. Two electrodes 2 to measure salinity of a food sample are protruded from the lower portion of the case assembly 1, and a temperature sensor (not shown) to measure temperature of the sample is installed within the electrodes 2.

Since the conventional salinity analyzer is not provided with any tool or means to allow a user to carry it, the user cannot safely and conveniently carry the salinity analyzer but carries the salinity analyzer under the condition the salinity analyzer together with other articles is contained in a bag or a case, thereby causing damage to main parts of the salinity analyzer.

Further, the conventional salinity analyzer is provided with an ON/OFF switch (not shown). In order to use the salinity analyzer, the user presses the ON/OFF switch so as to apply power to a circuit board, and then after measurement of salinity, the user re-presses the ON/OFF switch so as to cut off power to the circuit board.

The user frequently stores or carries the conventional salinity analyzer under the condition that the power of the salinity analyzer is not turned off through user's carelessness after the measurement of salinity of the food sample. In this case, power of a battery is continuously consumed, and thus the battery may be easily discharged.

Further, the temperature sensor to measure the temperature of a food sample is installed within the electrodes 2 of the conventional salinity analyzer. Therefore, in order to measure the temperature of the food sample, heat of the food sample is firstly transmitted to the electrode 2, and then the heat of the electrodes 2 is transmitted again to the temperature sensor.

Since the temperature sensor cannot directly measure the temperature of the food sample, but can measure the temperature of the food sample via the electrode 2, sensing of the temperature of the food sample by the temperature sensor is considerably delayed, and thus correct and rapid measurement of the temperature of the food sample is difficult.

SUMMARY OF THE INVENTION

Therefore, the present invention has been made in view of the above problems, and it is an object of the present invention to provide a handheld salinity analyzer which is conveniently and safely portable.

It is a further object of the present invention to provide a handheld salinity analyzer which prevents power of a battery from be unnecessarily consumed.

It is another object of the present invention to provide a handheld salinity analyzer which achieves rapid and correct measurement of temperature of a food sample.

It is another object of the present invention to provide a handheld salinity analyzer which simply judges whether or not measured salinity of a food sample is less than or more than a set value.

It is yet another object of the present invention to provide a handheld salinity analyzer which diffuses light of a light emitting lamp, when the light emitting lamp is turned on, throughout one end of a body cover.

In accordance with the present invention, the above and other objects can be accomplished by the provision of a handheld salinity analyzer comprising a body formed in a hollow shape, and provided with a pressing part on the front surface thereof, a through hole formed at one side of the pressing part, a clip fixing part formed on the rear surface thereof, and a battery cover detachably provided at one side of the clip fixing part, a clip provided with one end connected to the clip fixing part of the body and the other end inserted into clothes or a bag, a circuit board installed within the body, and provided with a button formed thereon so as to be opposite to the pressing part and a display part connected thereto so as to be opposite to the through hole, a battery installed in the body at a position within the battery cover and connected to the circuit board, a cell block provided with one end inserted into one end of the body so as to be opposite to one end of the circuit board and the other end on which a projecting part and a depressed part are formed, a salinity sensor hole connected to the circuit board being formed through the projecting part and a temperature sensor hole connected to the circuit board being formed through the depressed part, a salinity sensor inserted into the salinity sensor hole of the cell block, and provided with one end connected to the circuit board and the other end contacting a food sample to measure salinity of the food sample, a temperature sensor inserted into the temperature sensor hole of the cell block, and provided with one end connected to the circuit board and the other end exposed to the outside of the depressed part so as to directly contact the food sample, an ON/OFF switch installed on the end of the body in opposite to the cell block, connected to the circuit board and the battery, and provided with an end protruded to the outside of the end of the body, a light emitting lamp installed at one side of the ON/OFF switch, and connected to the circuit board, and a body cover connected to the end of the body provided with the ON/OFF switch or to the cell block, provided with an operating piece formed therein so as to apply force to the ON/OFF switch, when the body cover is connected to the end of the body provided with the ON/OFF switch, and to remove the force from the ON/OFF switch, when the body cover is separated from the end of the body.

The depressed part of the cell block may include a first depression part, in which a pressing end of the operating piece is located, when the body cover is connected to the cell block, and a second depression part, in which one end of the temperature sensor, protruding to the outside, is located, and inclined at one side of the first depression part so as to prevent interference between the end of the temperature sensor and the pressing end, when the pressing end of the operating piece is located in the first depression part.

The light emitting lamp may emit light of different colors when the measured salinity of the food sample is less than a set value and when the measured salinity of the food sample is more than the set value.

The body cover may be made of a transparent material, and a plurality of diffused reflection protrusions to diffuse light when the light emitting lamp emits light may be formed on the inner surface of the body cover.

The operating piece of the body cover may be fixed to the body cover such that the operating piece occupies a space corresponding to half of the inner space of the body cover so as to secure an entrance space, which the projecting part of the cell block and the salinity sensor enter, when the body cover is connected to the end of the body, at which the ON/OFF switch is located, the pressing end of the operating piece may press the ON/OFF switch to operate the ON/OFF switch, when the body cover is separated from the end of the body, the pressing of the ON/OFF switch by the pressing end of the operating piece may be released, and when the body cover is connected to the other end of the body, at which the sensors are located, the pressing end of the operating piece may be located in the first depression part of the cell block.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Detailed features and advantages of the present invention will be more apparent in the following description of a preferred embodiment thereof with reference to the accompanying drawings.

Figure 2:
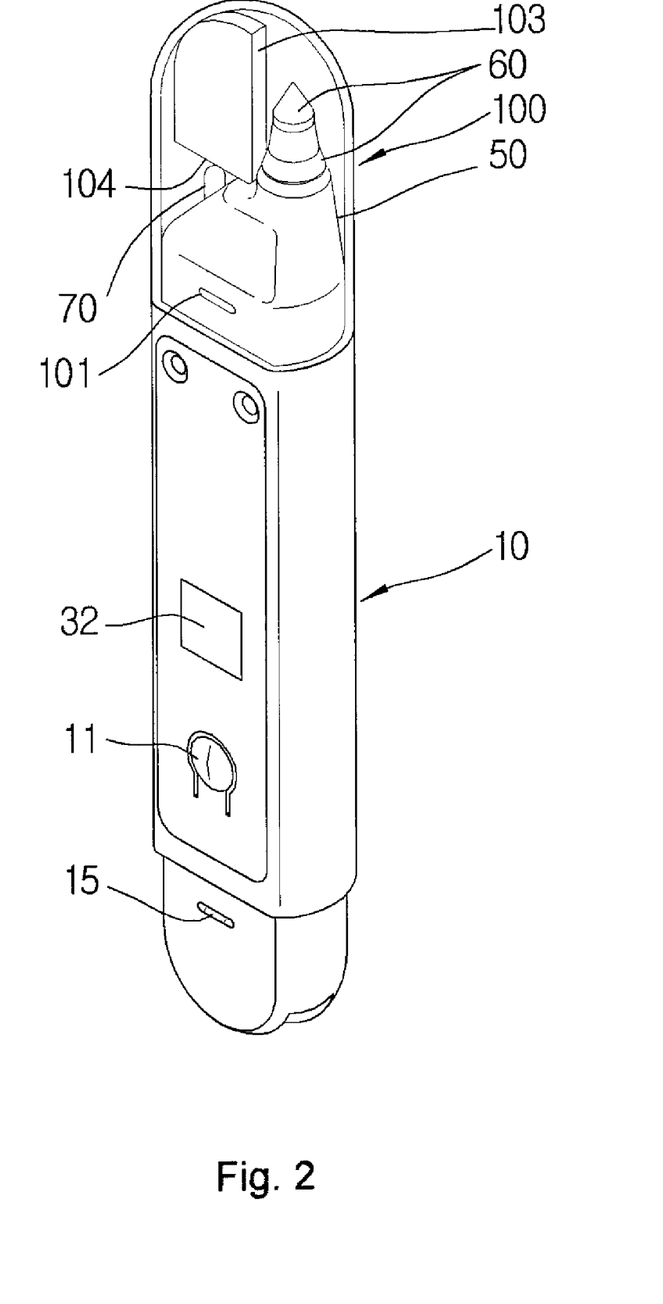
FIG. 2 is a schematic perspective view of a handheld salinity analyzer in accordance with the present invention.
Figure 3:
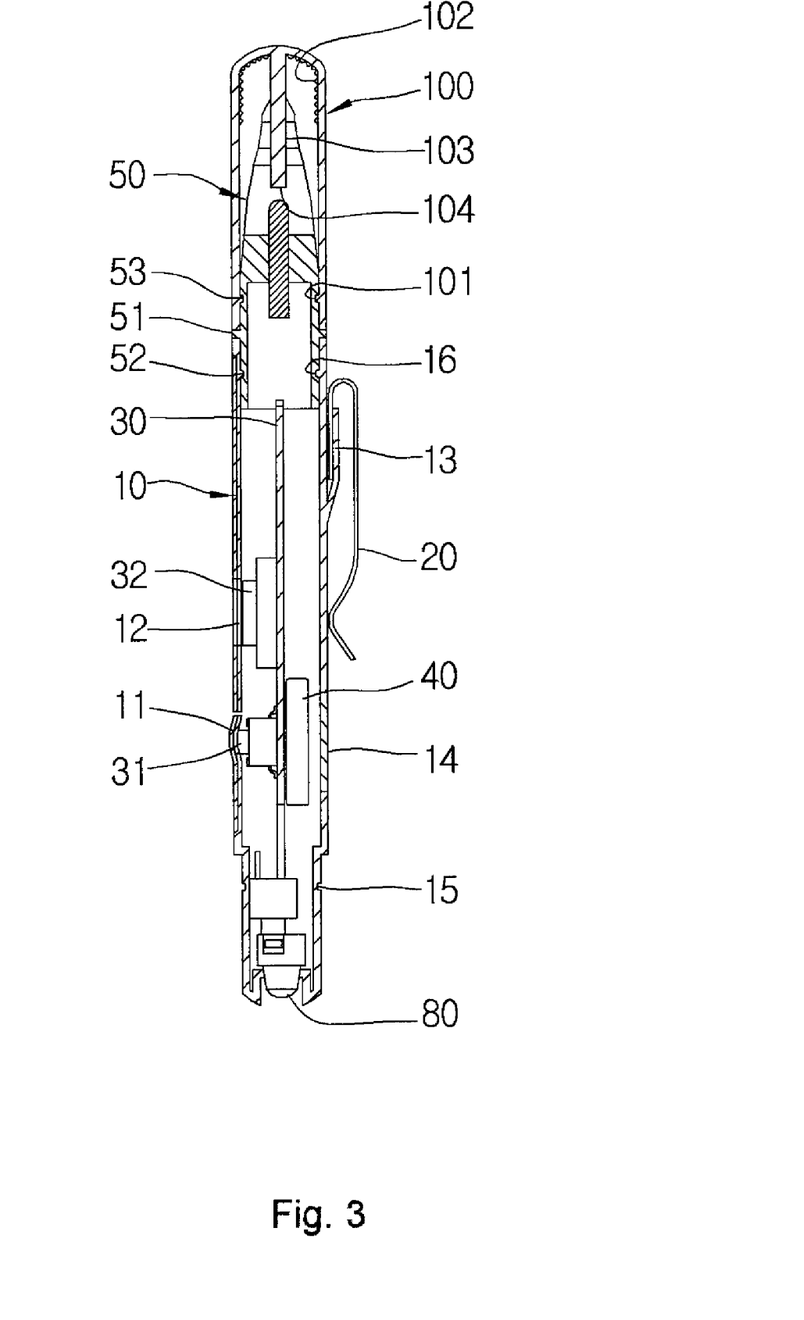
FIG. 3 is a schematic side sectional view of the handheld salinity analyzer.
Figure 4:
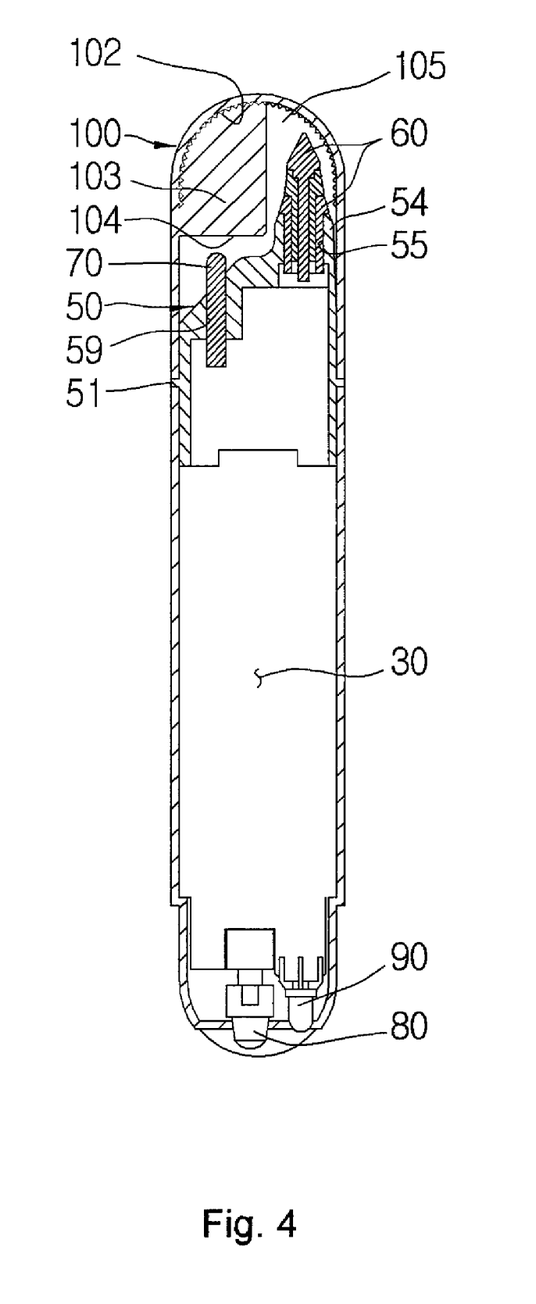
FIG. 4 is a schematic front sectional view of the handheld salinity analyzer.
Figure 5:
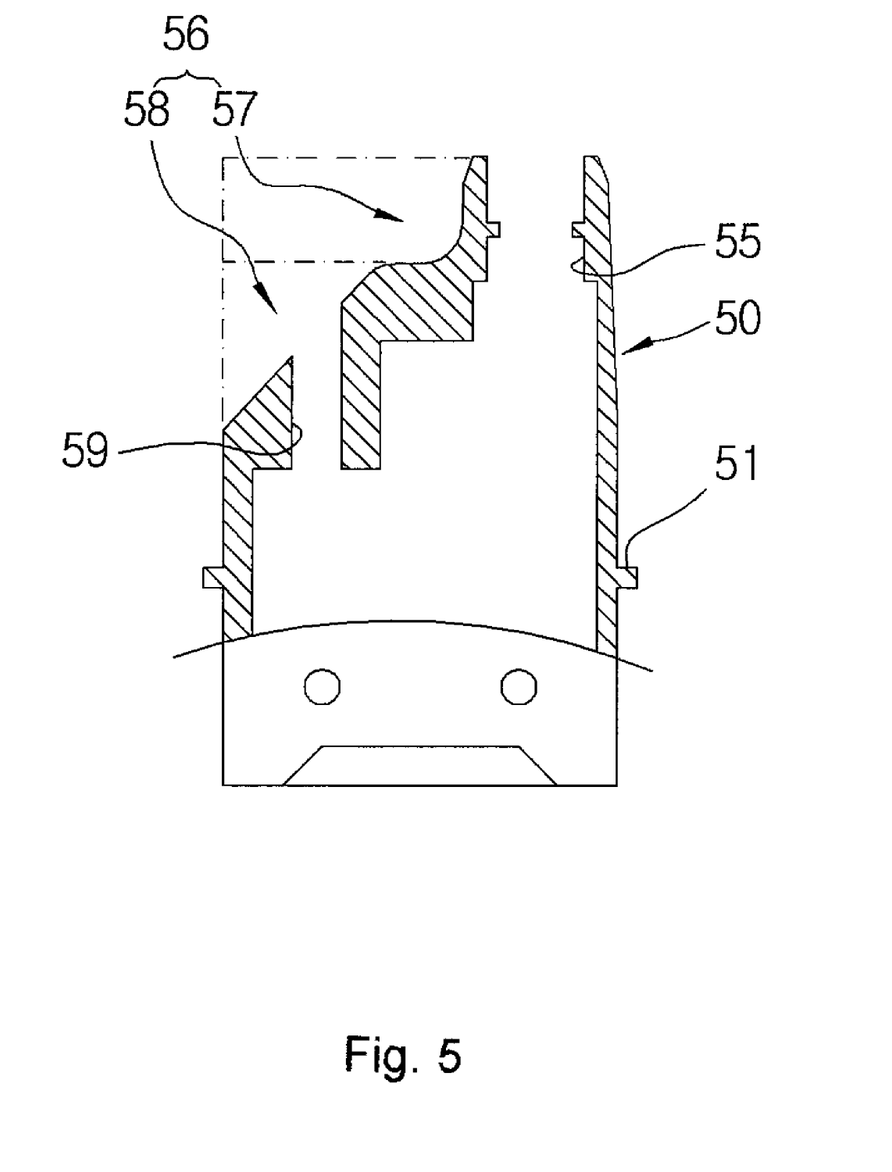
FIG. 5 is a schematic sectional view of a cell block extracted from the handheld salinity analyzer.
Figure 6:
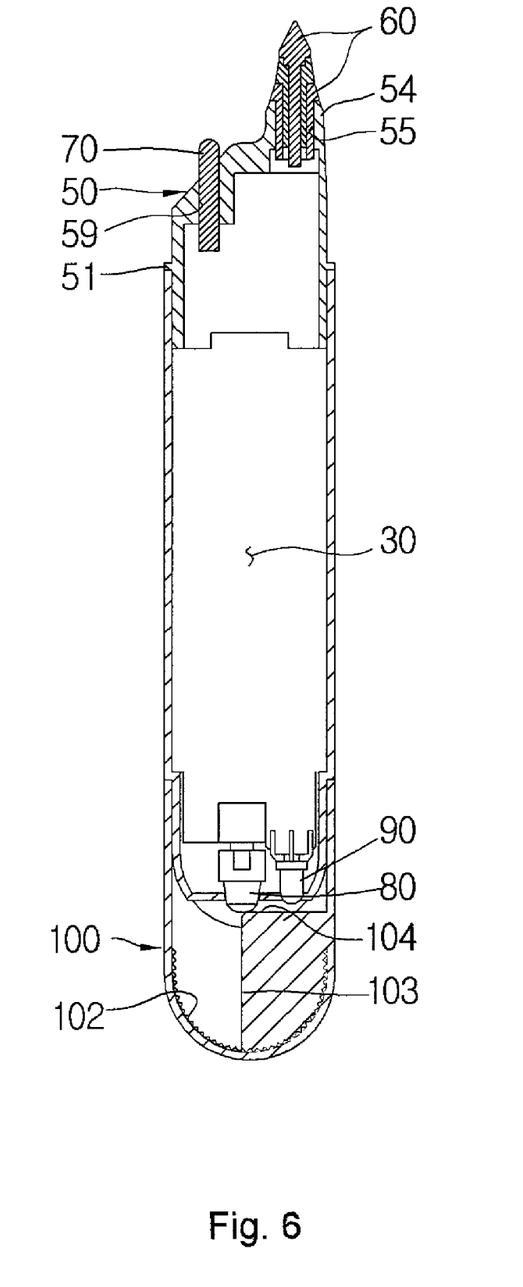
FIG. 6 is a schematic front sectional view illustrating the handheld salinity analyzer in use under the condition that a body cover is taken off and then is connected to an end of a body provided with an ON/OFF switch.
Figure 7:
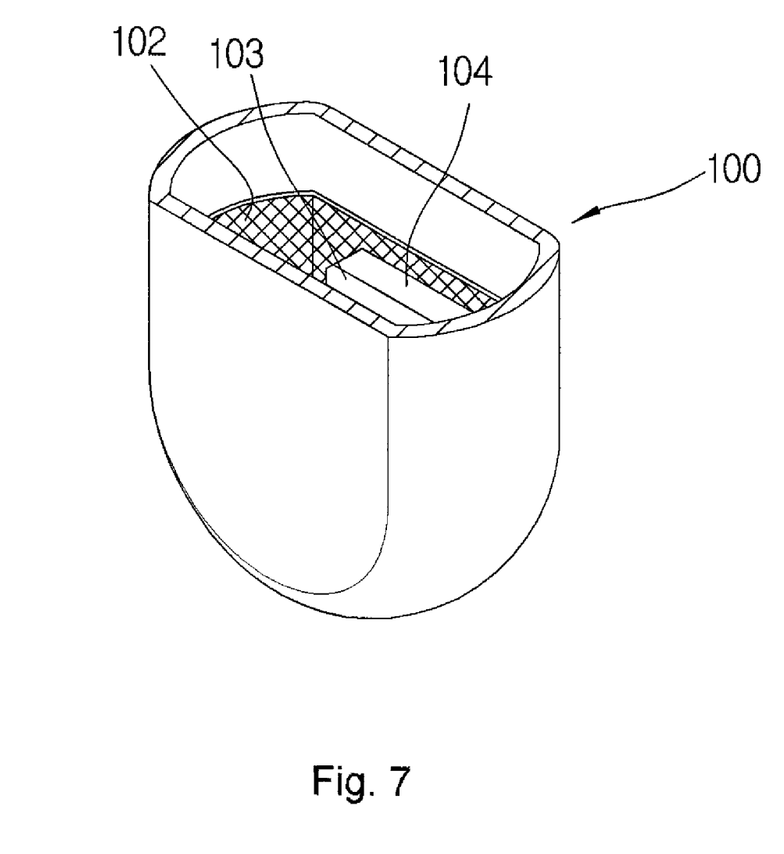
FIG. 7 is a schematic perspective view illustrating the inside of the body cover.

FIG. 2 is a schematic perspective view of a handheld salinity analyzer in accordance with the present invention, FIG. 3 is a schematic side sectional view of the handheld salinity analyzer, FIG. 4 is a schematic front sectional view of the handheld salinity analyzer, FIG. 5 is a schematic sectional view of a cell block extracted from the handheld salinity analyzer, FIG. 6 is a schematic front sectional view illustrating the handheld salinity analyzer in use under the condition that a body cover is taken off and then is connected to an end of a body provided with an ON/OFF switch, and FIG. 7 is a schematic perspective view illustrating the inside of the body cover.

The handheld salinity analyzer in accordance with the present invention includes a body 10, a clip 20, a circuit board 30, a battery 40, a cell block 50, a salinity sensor 60, a temperature sensor 70, an ON/OFF switch 80, a light emitting lamp 90, and a body cover 100.

The body 10 is formed in a hollow shape, and is provided with a pressing part 11 on the front surface thereof, and a through hole 12 formed at one side of the pressing part 11. A clip fixing part 13 is formed on the rear surface of the body 10, and a battery cover 14 is detachably provided at one side of the clip fixing part 13.

Attachable and detachable grooves 15 are formed on the outer surface of one end of the body 10 such that attachable and detachable protrusions 101 are attached to and detached from the attachable and detachable grooves 15, and attachable and detachable protrusions 16 are protruded from the inner surface of the other end of the body 10 such that the attachable and detachable protrusions 16 are attached to and detached from first attachable and detachable grooves 52 of the cell block 50, which will be described later.

The clip 20 is provided with one end connected to the clip fixing part 13 of the body 10 and the other end such as clothes or a bag.

Therefore, a user may conveniently carry the handheld salinity analyzer of the present invention on clothes or a pocket of a bag just like a writing instrument.

The circuit board 30 is installed within the body 10, and is provided with a button 31 formed thereon so as to be opposite to the pressing part 11 and a display part 32 connected thereto so as to be opposite to the through hole 12 of the body 10. Therefore, when the user presses the pressing part 11 of the body 10, the button 31 is pressed and data is input to the circuit board 30. Further, a measured salinity value is displayed through the display part 32 such that the user may read the measured salinity value.

The battery 40 is installed in the body 10 at a position within the battery cover 14, and is connected to the circuit board 30 so as to supply power to the circuit board 30.

The cell block 50 is provided with one end inserted into one end of the body 10 so as to be opposite to one end of the circuit board 30, and is provided with the other end exposed to the outside of the body 10. A projecting part 54 and a depressed part 56 are formed on the other end of the cell block 50. A salinity sensor hole 55 connected to the circuit board 30 is formed through the projecting part 54, and a temperature sensor hole 59 connected to the circuit board 30 is formed through the depressed part 56.

The first attachable and detachable grooves 52 connected to the attachable and detachable protrusions 16 of the body 10 and second attachable and detachable grooves 53 connected to the attachable and detachable protrusions 101 of the body cover 100 are formed on the outer surface of the cell block 50. A flange 51, which is supported by the end of the body 10 to restrict the insertion of the cell block 50 when the cell block 50 is inserted into the end of the body 10, is formed around the outer surface of the cell block 50 between the first attachable and detachable grooves 52 and the second attachable and detachable grooves 53.

The depressed part 56 includes a first depression part 57 and a second depression part 58. A pressing end 104 of an operating piece 103 is located in the first depression part 57, when the body cover 100 is connected to the other end of the body 10 provided with the cell block 50. One end of the temperature sensor 70, protruding to the outside, is located in the second depression part 58, and the second depression part 58 is inclined at one side of the first depression part 57 so as to prevent interference between the end of the temperature sensor 70 and the pressing end 104, when the pressing end 104 of the operating piece 103 is located in the first depression part 57.

The salinity sensor 60 is inserted into the salinity sensor hole 55 of the cell block 50, and one end of the salinity sensor 60 is connected to the circuit board 30 and the other end of the salinity sensor 60 contacts a food sample to measure salinity of the food sample.

The temperature sensor 70 is inserted into the temperature sensor hole 59 of the cell block 50, and one end of the temperature sensor 70 is connected to the circuit board 30 and the other end of the temperature sensor 70 is exposed to the outside of the second depression part 58 and thus directly contacts the food sample.

The ON/OFF switch 80 is installed on the end of the body 10 in opposite to the cell block 50 and is connected to the circuit board 30 and the battery 40, and one end of the ON/OFF switch 80 is protruded to the outside of the end of the body 10. When external force is applied to the end of the ON/OFF switch 80, power of the battery 40 is supplied to the circuit board 30 and thus the salinity analyzer is operated, and when the external force is removed from the ON/OFF switch 80, the ON/OFF switch 80 is turned off and thus power supplied to the circuit board 30 is cut off.

The light emitting lamp 90 is installed at one side of the ON/OFF switch 80, and is connected to the circuit board 30. The light emitting lamp 90 emits light of different colors, if the measured salinity of the food sample is less than a set value and if the measured salinity of the food sample is more than the set value. Hereinafter, the light emitting lamp 90 will be described in more detail.

A blue LED (not shown) and a red LED (not shown) are installed in the light emitting lamp 90, and are connected to the circuit board 30. A reference salinity value is set in the circuit board 30 of the handheld salinity analyzer. Further, the circuit board 30 is programmed such that salinity of a food sample is measured, and when the measured salinity is less than the set value, the blue LED is turned on, and when the measured salinity is more than the set value, the red LED is turned on.

Therefore, when the measured salinity of the food sample is less than the set value, the light emitting lamp 90 emits blue light, and when the measured salinity of the food sample is more than the set value, the light emitting lamp 90 emits red light.

The body cover 100 is connected to the end of the body 10 provided with the ON/OFF switch 80 or to the cell block 50. The body cover 100 is provided with the operating piece 103 formed therein so as to apply force to the ON/OFF switch 80, when the body cover 100 is connected to the end of the body 10 provided with the ON/OFF switch 80, and to remove the force from the ON/OFF switch 80, when the body cover 100 is separated from the end of the body 10.

Such a body cover 100 is made of a transparent material, and a plurality of diffused reflection protrusions 102 to diffuse light emitted from the light emitting lamp 90 when the light emitting lamp 90 is turned on is formed on the inner surface of the body cover 100. Further, the attachable and detachable protrusions 101, which are connected to the attachable and detachable grooves 15 of the body 10 or the second attachable and detachable grooves 53 of the cell block 50, protrude from the inner surface of an entrance of the body cover 100.

The operating piece 103 of the body cover 100 is fixed to the body cover 100 such that the operating piece 103 occupies a space corresponding to half of the inner space of the body cover 100 so as to secure an entrance space 105, which the projecting part 54 of the cell block 50 and the salinity sensor 60 enter.

Therefore, when the body cover 100 is connected to one end of the body 10, at which the ON/OFF switch 80 is located, the pressing end 104 of the operating piece 103 presses the ON/OFF switch 80 to operate the ON/OFF switch 80, and when the body cover 100 is separated from the end of the body 10, the pressing of the ON/OFF switch 80 by the pressing end 104 of the operating piece 103 is released. Further, when the body cover 100 is connected to the other end of the body 10, at which the sensors are located, the pressing end 104 of the operating piece 103 is located in the first depression part 57 of the cell block 50.

The above-described handheld salinity analyzer of the present invention, as shown in FIGS. 2 to 4, is carried by a user such that the clip 20 is inserted into a pocket of clothes or a bag under the condition that the body cover 100 is connected to the cell block 50. When the attachable and detachable protrusions 16 of the body cover 100 are connected to the second attachable and detachable grooves of the cell block 50, the pressing end 104 of the operating piece 103 is located in the first depression part 57 of the cell block 50. Here, the end of the temperature sensor 70 is located in the second depression part 58, and the projecting part 54 of the cell block 50 and the salinity sensor 60 are located in the entrance space 105 of the body cover 100.

In order to use the handheld salinity analyzer, the body cover 100 is separated from the cell block 50, and then is inserted into the end of the body 10 provided with the ON/OFF switch 80. Here, the attachable and detachable protrusions 101 of the body cover 100 are connected to the attachable and detachable grooves 15 of the body 10.

When the body cover 100 is connected to the end of the body 10 in this manner, the pressing end 104 of the operating piece 103 presses the ON/OFF switch 80, as shown in FIG. 7, and thereby the ON/OFF switch 80 is turned on and the handheld salinity analyzer is operated. When the handheld salinity analyzer is operated, the salinity sensor 60 and the temperature sensor 70 are dipped in a food sample so as to measure salinity of the food sample.

When measurement of the salinity of the food sample has been completed, the salinity sensor 60, the temperature sensor 70, and the cell block 50, which were dipped in the food sample, are washed, the body cover 100 is separated from the end of the body 10 provided with the ON/OFF switch 80, and the separated body cover 100 is connected to the other end of the body 100 provided with the cell block 50. Here, when the body cover 100 is separated from the body 10, the pressing of the ON/OFF switch 80 by the pressing end 104 of the operating piece 103 is released, and the ON/OFF switch 80 is turned off, thereby cutting-off power of the battery 40.

As apparent from the above description, the handheld salinity analyzer of the present invention has advantages, as follows.

First, in the handheld salinity analyzer of the present invention, one end of the clip 20 is fixed to the rear surface of the body 10. When the other end of the clip 20 is inserted into an entrance of a pocket of clothes or a bag of a user, the user may conveniently and safely carry the handheld salinity analyzer of the present invention just like a pen, and easily use the handheld salinity analyzer at any place.

Second, when the body cover 100 is separated from one end of the body 10 provided with the cell block 50 and then is connected to the other end of the body provided with the ON/OFF switch 80, the pressing end 104 of the operating piece 103 presses the ON/OFF switch 80, and thus the handheld salinity analyzer is operated.

When the body cover 100 is separated from the body 10 so as to be connected to the cell block 50 after use of the handheld salinity analyzer, the pressing of the ON/OFF switch 80 by the pressing end 104 of the operating piece 103 is released, and the ON/OFF switch 80 is turned off. Therefore, since, when the body cover 100 is connected to the cell block 50 so as to keep the salinity sensor after use, the ON/OFF switch 80 is automatically turned off, it is possible to solve the conventional problem, i.e., unnecessary consumption of power of the battery 40 as the salinity sensor is kept under the condition that the ON/OFF switch 80 is not turned off.

Third, in the handheld salinity analyzer of the present invention, the end of the temperature sensor 70 is protruded toward the second depression part 58. Therefore, when the end of the cell block 50 is dipped in a food sample, the end of the temperature sensor 70 exposed to the outside directly contacts the sample, thereby rapidly and correctly measuring a temperature of the sample.

Fourth, when the measured salinity of the food sample is less than a set value, the light emitting lamp 90 emits blue light through the blue LED, and when the measured salinity of the food sample is more than the set value, the light emitting lamp 90 emits red light through the red LED. Therefore, a user can easily judge whether or not the salinity of the food sample is less than or more than the proper set value without the confirmation of numbers displayed on the display part 32.

Fifth, the body cover 100 is made of a transparent material, and a plurality of diffused reflection protrusions 102 to diffuse light emitted from the light emitting lamp 90 when the light emitting lamp 90 is turned on is formed on the inner surface of the body cover 100. Therefore, the light emitted from the light emitting lamp is diffused due to collision with the plurality of diffused reflection protrusions 102, and thus is diffused throughout the end of the body cover 100, thereby improving the design of the handheld salinity analyzer in use and allowing the user to correctly confirm the light emitted from the light emitting lamp 90.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A handheld salinity analyzer comprising:
    a body formed in a hollow shape, and provided with a pressing part on the front surface thereof, a through hole formed at one side of the pressing part, a clip fixing part formed on the rear surface thereof, and a battery cover detachably provided at one side of the clip fixing part;
    a clip provided with one end connected to the clip fixing part of the body and the other end inserted into clothes or a bag;
    a circuit board installed within the body, and provided with a button formed thereon so as to be opposite to the pressing part and a display part connected thereto so as to be opposite to the through hole;
    a battery installed in the body at a position within the battery cover and connected to the circuit board;
    a cell block provided with one end inserted into one end of the body so as to be opposite to one end of the circuit board and the other end on which a projecting part and a depressed part are formed, having a salinity sensor hole connected to the circuit board being formed through the projecting part and a temperature sensor hole connected to the circuit board being formed through the depressed part;
    a salinity sensor inserted into the salinity sensor hole of the cell block, and provided with one end connected to the circuit board and the other end contacting a food sample to measure salinity of the food sample;
    a temperature sensor inserted into the temperature sensor hole of the cell block, and provided with one end connected to the circuit board and the other end exposed to the outside of the depressed part so as to directly contact the food sample;
    an ON/OFF switch installed on the end of the body in opposite to the cell block, connected to the circuit board and the battery, and provided with an end protruded to the outside of the end of the body;
    a light emitting lamp installed at one side of the ON/OFF switch, and connected to the circuit board; and
    a body cover connected to the end of the body provided with the ON/OFF switch or to the cell block, provided with an operating piece formed therein so as to apply force to the ON/OFF switch, when the body cover is connected to the end of the body provided with the ON/OFF switch, and to remove the force from the ON/OFF switch, when the body cover is separated from the end of the body.

2. The handheld salinity analyzer according to claim 1, wherein the depressed part of the cell block includes a first depression part, in which a pressing end of the operating piece is located, when the body cover is connected to the cell block, and a second depression part, in which one end of the temperature sensor, protruding to the outside, is located, and inclined at one side of the first depression part so as to prevent interference between the end of the temperature sensor and the pressing end, when the pressing end of the operating piece is located in the first depression part.

3. The handheld salinity analyzer according to claim 1, wherein the light emitting lamp emits light of different colors when the measured salinity of the food sample is less than a set value and when the measured salinity of the food sample is more than the set value.

4. The handheld salinity analyzer according to claim 1, wherein the body cover is made of a transparent material, and a plurality of diffused reflection protrusions to diffuse light when the light emitting lamp emits light is formed on the inner surface of the body cover.

5. The handheld salinity analyzer according to claim 2, wherein:
    the operating piece of the body cover is fixed to the body cover such that the operating piece occupies a space corresponding to half of the inner space of the body cover so as to secure an entrance space, which the projecting part of the cell block and the salinity sensor enter; and
    when the body cover is connected to the end of the body, at which the ON/OFF switch is located, the pressing end of the operating piece presses the ON/OFF switch to operate the ON/OFF switch, when the body cover is separated from the end of the body, the pressing of the ON/OFF switch by the pressing end of the operating piece is released, and when the body cover is connected to the other end of the body, at which the sensors are located, the pressing end of the operating piece is located in the first depression part of the cell block.

* * * * *